(12) United States Patent
Araci et al.

(10) Patent No.: US 10,219,696 B2
(45) Date of Patent: *Mar. 5, 2019

(54) IMPLANTABLE PRESSURE SENSORS FOR TELEMETRIC MEASUREMENTS THROUGH BODILY TISSUES

(71) Applicant: The Board of Trustees of the Leland Stanford Junior University, Palo Alto, CA (US)

(72) Inventors: Ismail E Araci, Palo Alto, CA (US); Stephen R Quake, Stanford, CA (US); Melanie Hayden Gephart, San Mateo, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 537 days.

This patent is subject to a terminal disclaimer.

(21) Appl. No.: 14/860,370

(22) Filed: Sep. 21, 2015

(65) Prior Publication Data
US 2016/0007851 A1    Jan. 14, 2016

Related U.S. Application Data

(63) Continuation-in-part of application No. 14/771,576, filed as application No. PCT/US2014/019660 on Feb. 28, 2014, now Pat. No. 10,016,132.

(Continued)

(51) Int. Cl.
*A61B 3/16*    (2006.01)
*A61B 5/03*    (2006.01)
(Continued)

(52) U.S. Cl.
CPC .............. *A61B 3/16* (2013.01); *A61B 8/0841* (2013.01); *A61B 5/0071* (2013.01); *A61B 5/031* (2013.01);
(Continued)

(58) Field of Classification Search
CPC ... A61B 3/16; A61B 5/031; A61B 5/03–5/038
See application file for complete search history.

(56) References Cited

U.S. PATENT DOCUMENTS 5,433,701 A    7/1995    Rubinstein
5,671,737 A    9/1997    Harosi
(Continued)

FOREIGN PATENT DOCUMENTS

JP    2002277291    *    9/2002    ............. G01D 21/00

OTHER PUBLICATIONS

Lin et al. "Intraocular Pressure Sensors: New Approaches for Real-Time Intraocular Pressure Measurement Using a Purely Microfluidic Chip" Oct. 2012.*

(Continued)

*Primary Examiner* — Adam J Eiseman
(74) *Attorney, Agent, or Firm* — Lumen Patent Firm

(57) ABSTRACT

Continuous pressure sensing is important for patients with several different conditions. We provide an implantable sensor, based on microfluidic principles, which in one example has 1 mmHg limit of detection, high sensitivity and excellent reproducibility. This sensor has an optical interface, which enables pressure to be read with, for example, a cell phone camera. The design and fabrication, along with the option of self-monitoring are promising steps toward better patient care and treatment.

22 Claims, 17 Drawing Sheets

Related U.S. Application Data

(60) Provisional application No. 62/061,658, filed on Oct. 8, 2014, provisional application No. 61/773,963, filed on Mar. 7, 2013.

(51) Int. Cl.
*A61B 8/08* (2006.01)
*A61B 5/00* (2006.01)

(52) U.S. Cl.
CPC ............... *A61B 5/036* (2013.01); *A61B 5/72* (2013.01); *A61B 2562/0247* (2013.01)

(56) References Cited

U.S. PATENT DOCUMENTS

| | | | |
|---|---|---|---|
| 6,010,461 A | 1/2000 | Haniff | |
| 6,575,026 B1* | 6/2003 | DeBar | G01L 7/20 73/202 |
| 7,252,006 B2 | 8/2007 | Tai | |
| 7,452,075 B2 | 11/2008 | Iuliano | |
| 8,246,569 B1 | 8/2012 | Meng | |
| 8,850,895 B2 | 10/2014 | Yan | |
| 2003/0097052 A1* | 5/2003 | Ahmed | A61B 3/16 600/399 |
| 2007/0019156 A1* | 1/2007 | Fink | A61B 3/16 351/200 |
| 2008/0139959 A1* | 6/2008 | Miethke | A61B 5/0031 600/561 |
| 2009/0069648 A1 | 3/2009 | Irazoqui | |
| 2009/0096988 A1 | 4/2009 | Fink | |
| 2010/0245570 A1* | 9/2010 | Riedel | A61N 1/39 348/143 |
| 2010/0256465 A1* | 10/2010 | Bernstein | A61B 5/1438 600/309 |
| 2012/0302861 A1* | 11/2012 | Marshall | A61B 3/16 600/398 |
| 2014/0371624 A1* | 12/2014 | Ziaie | A61B 5/0031 600/561 |

OTHER PUBLICATIONS

Lin et al. 2012. Intraocular pressure sensors: new approaches for real-time intraocular pressure measurement using a purely microfluidic chip. 16th Int. Conf. on Miniaturized Systems for Chemistry and Life Sciences, Oct. 28, 2012.

Yan (2011) An unpowered, wireless contact lens pressure sensor for point-of-care glaucoma diagnosis. Conf Proc IEEE Eng Med Biol Soc. 2011;2011:2522-5.

* cited by examiner

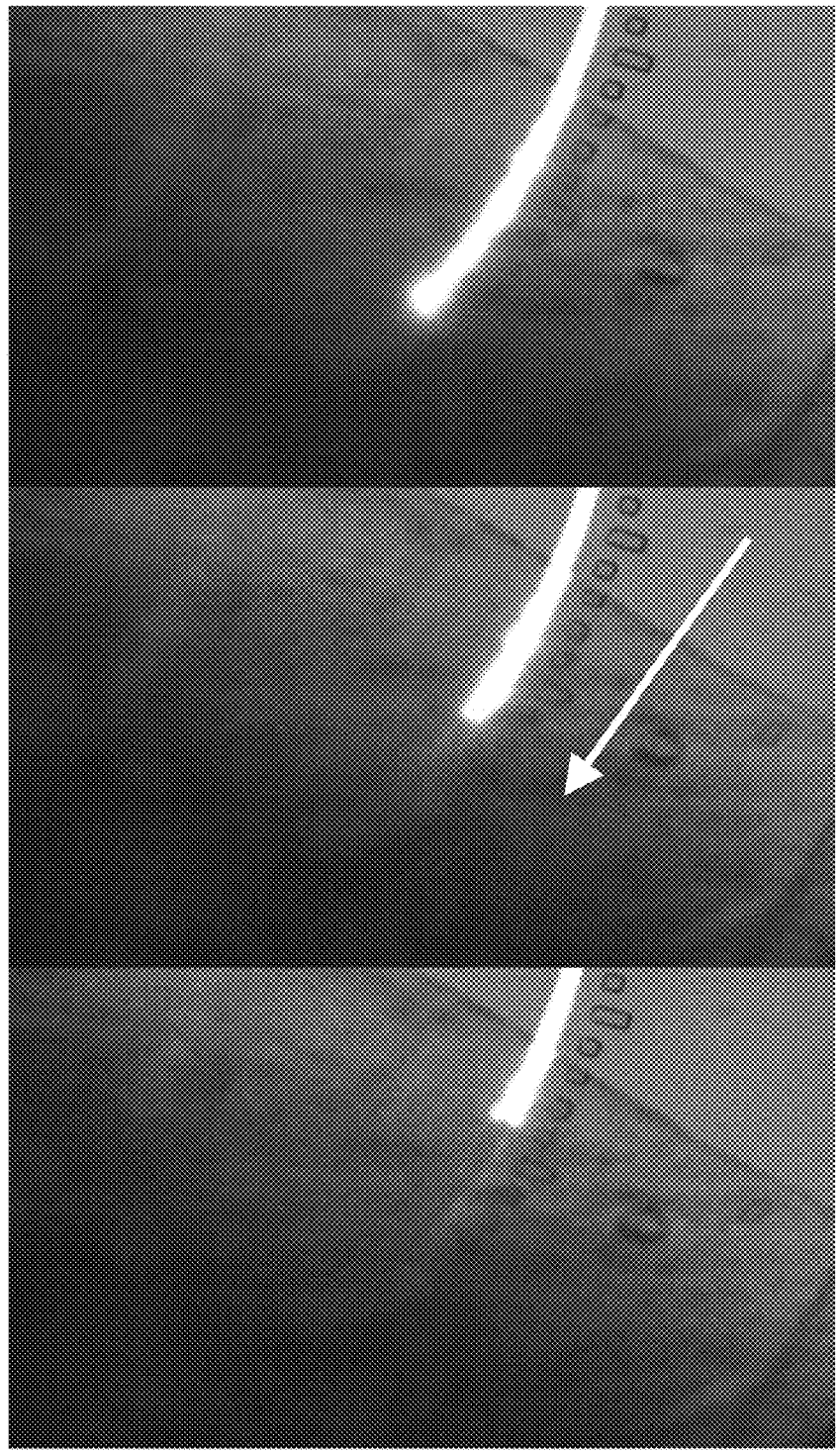

IMPLANTABLE PRESSURE SENSORS FOR TELEMETRIC MEASUREMENTS THROUGH BODILY TISSUES

CROSS-REFERENCE TO RELATED APPLICATIONS

This application claims priority from U.S. Provisional Patent Application 62/061,658 filed Oct. 8, 2014, which is incorporated herein by reference. This application is a continuation-in-part of U.S. patent application Ser. No. 14/771,576 filed Aug. 31, 2015, which is incorporated herein by reference. U.S. patent application Ser. No. 14/771,576 filed Aug. 31, 2015 claims the benefit of and is a 371 application of PCT Patent Application PCT/US2014/019660 filed Feb. 28, 2014. PCT Patent Application PCT/US2014/019660 filed Feb. 28, 2014 claims the benefit of U.S. provisional application 61/773,963 filed Mar. 7, 2013.

FIELD OF THE INVENTION

This invention relates to implantable micro-fluidic monitoring devices, systems and methods. In particular, the invention relates to passive pressure monitoring implants with an external readout mechanism for use in organs (e.g. brain, heart, bladder, etc.) where telemetric measurements are needed.

BACKGROUND OF THE INVENTION

Continuous pressure sensing is important for patients with several different conditions. For example, hydrocephalus is characterized by abnormal accumulation of cerebrospinal fluid (CSF) in the brain, which leads to increased intracranial pressure (ICP). As ICP levels become elevated, the risk for brain damage and death increases. Typically, shunts are used to release the increased ICP, but more than 50% of shunts become infected, blocked, disconnected, which necessitates additional surgeries to replace the shunt. When a shunt is suspected of malfunctioning, patients must undergo CT scans, which, over time, expose them to dangerous levels of radiation. At present, neurosurgeons have no way to test a shunt once it has been implanted. If the ICP can be measured in real time after the shunt is placed into the brain, the shunt functionality can be checked which will greatly reduce the amount of unnecessary tests and surgeries. The present invention advances the art by providing pressure sensors, which can be used telemetrically.

SUMMARY OF THE INVENTION

Implantable pressure sensors for telemetric measurements through bodily tissues are provided as a device, system and method. The sensor can provide measurement of pressure levels in brain, heart or other organs are necessary for patient monitoring. The sensors have the advantage that they can be used to decrease the amount of unnecessary tests and surgeries a patient will go through.

A sensing channel has a first open end and a second open end, and an inner diameter and could be made out of glass. A chamber is connected to the second open end of the sensing channel. A gas is disposed in the chamber and disposed through the second open end up to a region of the sensing channel. A fluid is disposed from the first open end up to the region of the sensing channel establishing a fluid-gas equilibrium pressure interface within the sensing channel, such that the inner diameter of the sensing channel is sized capable of holding the fluid within the sensing channel according to capillary forces. A porous tail channel is connected to the first open end of the sensing channel. The pressure monitoring device is configured to be implantable in a body, whereby the sensing channel and the chamber would be implanted under the tissue, and wherein the porous tail channel would interface with an organ liquid.

The sensing channel has positions or marking along the sensing channel represent different measures of fluid-gas equilibrium pressure interfaces. The inner diameter of the sensing channel is 1 mm to 300 mm or a cross section of the inner diameter of the sensing channel is 1 to 500 mm by 1 to 500 mm. The sensing channel has a length of 500 mm to 100 mm.

The porous tail channel has a length up to 1000 mm.

The ratio between the gas reservoir volume to the sensing channel cross section is in between 5 mm to $10^4$ mm. The sensing channel or the pressure monitoring device is coated to prevent leakage of the gas and/or fluid.

The sensing channel is a straight channel, a serpentine-like channel, or a circular-shaped channel. The fluid inside the sensing channel is mixed with IR fluorescent molecules.

In pressure monitoring system an imaging device is used to obtain an image of the sensing channel. An image analysis computer program is used to quantify the organ pressure from the obtained image and the established equilibrium pressure interface, and outputting the quantified organ pressure to a user. The fluid inside the sensing channel is mixed with IR fluorescent molecules and fluorescence imaging for detection of the gas liquid interface is realized by an IR sensitive camera through a skin tissue as the imaging device. The fluid inside the sensing channel is not mixed with any fluorescent molecules and an ultrasound imaging device is used for detection of the gas liquid interface through the skin tissue as the imaging device.

BRIEF DESCRIPTION OF THE DRAWINGS

FIGS. 15A-C show according to an exemplary embodiment of the invention a sensing region partially covered with a (in this case) chicken skin. The skin thickness is increasing in the direction of the arrow. The features can be seen in the beginning due to the bright field illumination in conjunction with the IR emission. Although the feature disappear as the skin thickness increase the interface can clearly be seen.

DETAILED DESCRIPTION

A first embodiment is detailed as a sensor to measure intra-ocular pressure. However, this operational concept, structural design and system is applicable for measuring pressure of various organs or body tissues such as of the brain, the heart, the bladder, etc. upon certain modifications to the first embodiment, which is further described in a second embodiment.

I. Intra-Ocular Pressure Sensor

Figure 1:
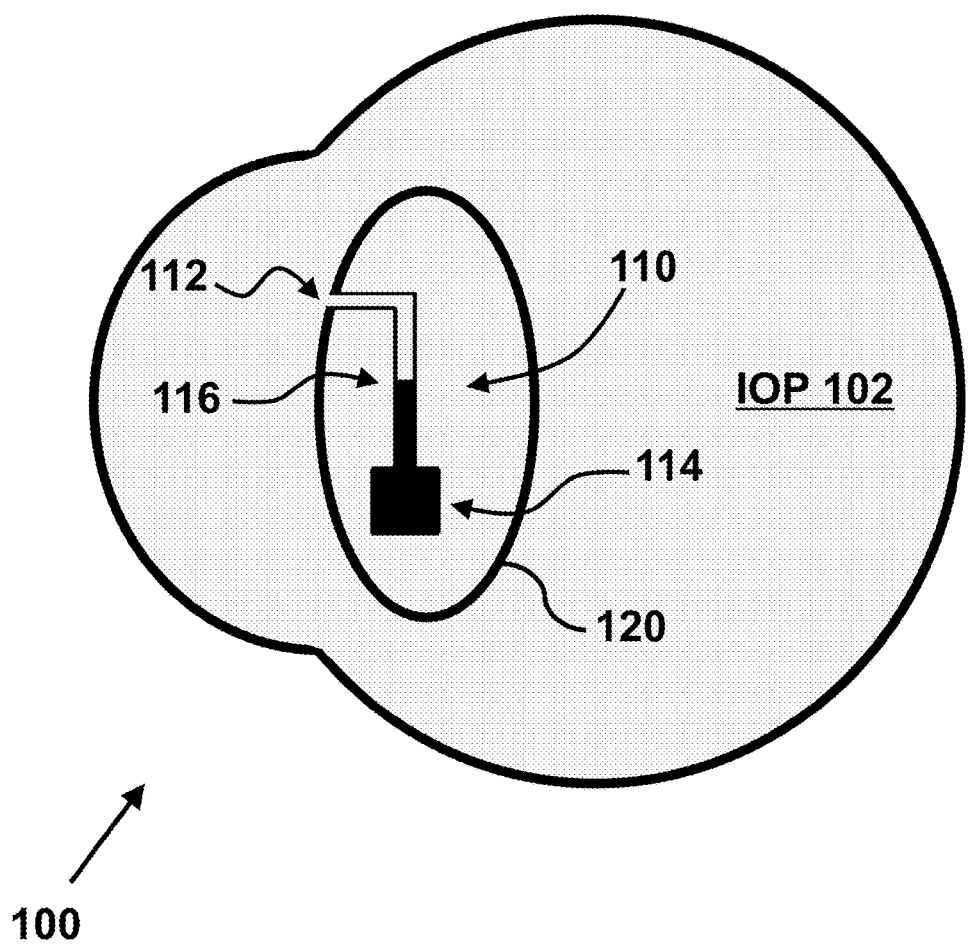
FIG. 1 shows an eye with an intra-ocular monitoring device according to an exemplary embodiment of the invention.

Embodiments of the invention use a passive Intra-Ocular-Pressure (IOP) sensor 110 based on the principles of microfluidic physics to monitor IOP (FIG. 1). The IOP sensor 110 can be chronically implanted into the eye 100 while incorporated in an intraocular lens (IOL) 120, which is routinely used for cataract surgery. Alternatively, it can be implanted as a standalone device in the anterior or posterior chambers of the eye. It can also be installed on a glaucoma drainage device.

In a first embodiment, the IOP sensor has a microfluidic channel 112 open to an aqueous intraocular liquid on one end and connected to a gas chamber or reservoir 114 on the other end (gas is indicated as black for illustration purposes). Capillary forces between the inner wall of the channel and the intraocular liquid and a positive intraocular pressure hold the liquid within at least part of the channel. Increased intraocular pressure 102 would drive the liquid further into the micro-channel 112, compressing the gas inside the reservoir until gas pressure is in equilibrium with liquid pressure as indicated by (gas-fluid) interface 116. Increased intraocular pressure causes the (gas-fluid) interface 116 to shift toward the channel's dead end (the gas reservoir), while decreasing the IOP causes a shift toward the channel opening.

Figure 2:
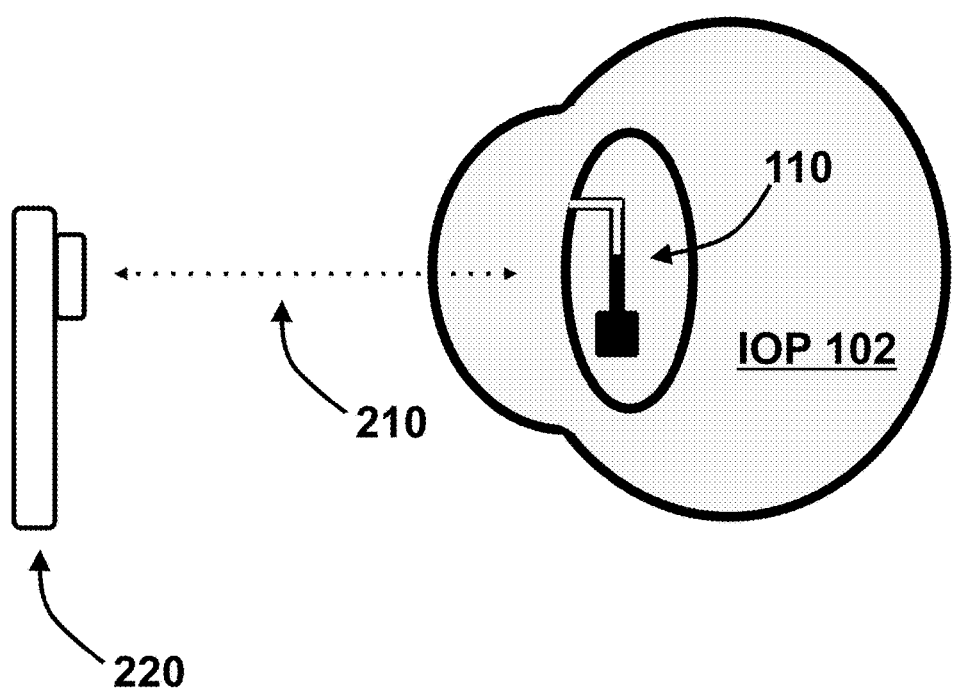
FIG. 2 shows an intra-ocular monitoring system according to an exemplary embodiment of the invention.

Intra-Ocular Pressure readout can be accomplished optically by passing light 210 with wavelength in the range of transparency to the ocular optical media through the eye structures and using a camera 220 to capture an image (FIG. 2). The readout can be performed through a cell phone camera 220, or other camera, equipped with an optical adaptor and image analysis software for detection of the liquid-air/gas interface position. The optical adaptor can be mounted on a cylindrical component designed to position the camera in front of the pupil and shade the eye, therefore eliciting pupil dilatation and exposing the peripherally located sensor. In one example, an iPhone was fitted with a molded plastic aspheric lens with 17 mm focal length or with a bi-convex lens with a 25 mm focal length. Alternatively, the position of the liquid-air/gas interface can be read by other camera-operated systems or easily observed by the ophthalmologist during routine eye examination with a slit lamp.

Figure 3:
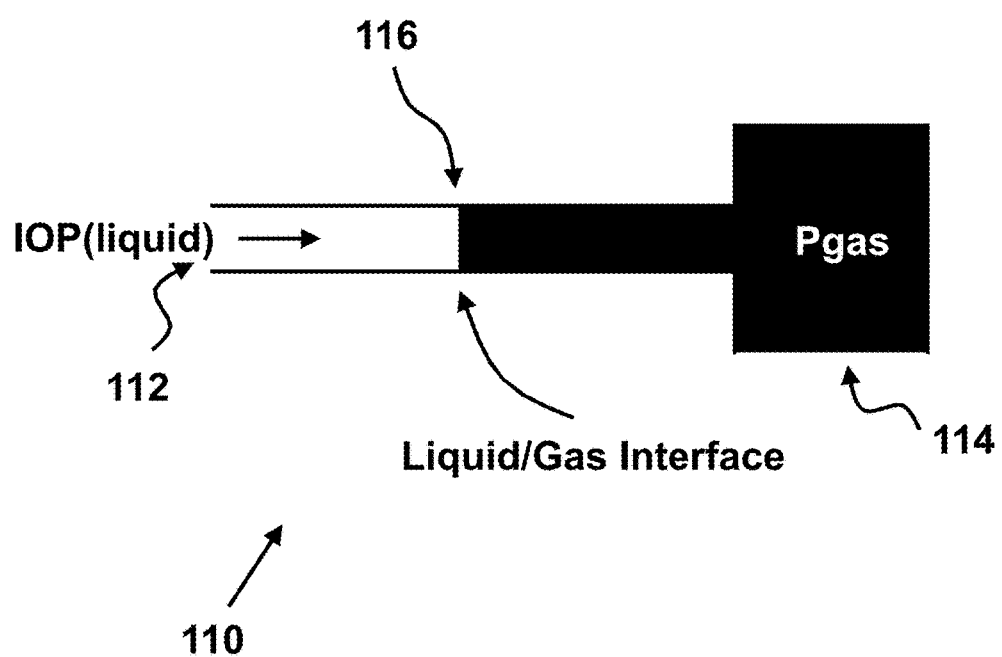
FIG. 3 shows a liquid-air or fluid-gas equilibrium pressure interface according to an exemplary embodiment of the invention.

FIG. 3 shows the operation of the IOP sensor 110. IOP is the liquid pressure, C is the capacitance due to device compliance, $\Delta P_{cap}$ is the capillary pressure drop, R is the fluidic resistance dependent on the channel geometry and $P_{gas}$ is the steady-state gas pressure.

In one example, the sensitivity of the sensor, defined as the displacement of the interface per 1 mmHg change in IOP, is proportional to the ratio between the total channel and reservoir volume to the channel cross section. For example, a sensitivity of about 57 µm/mmHg is expected in an IOP sensor with channel dimensions of 50×50×14,000 µm³ and a reservoir volume of 500×500×300 µm³.

Figure 4:
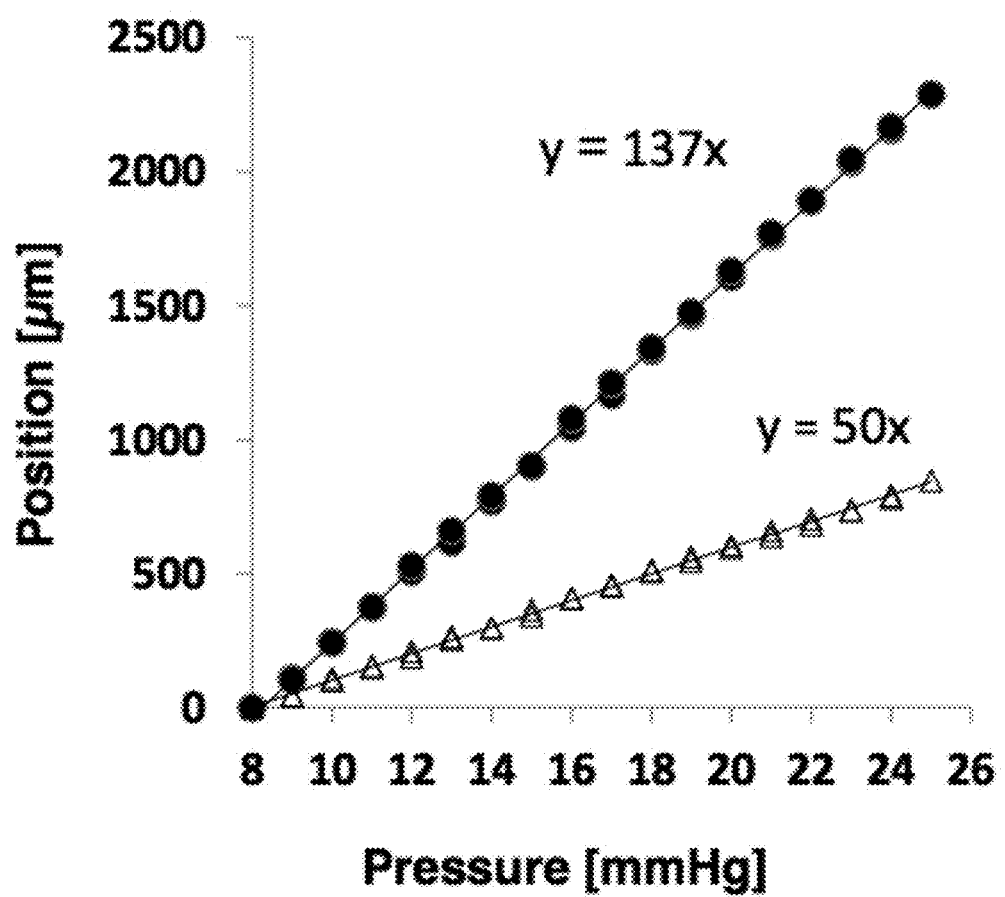
FIG. 4 shows measurements of pressure versus position along the channel according to an exemplary embodiment of the invention.
Figure 5:
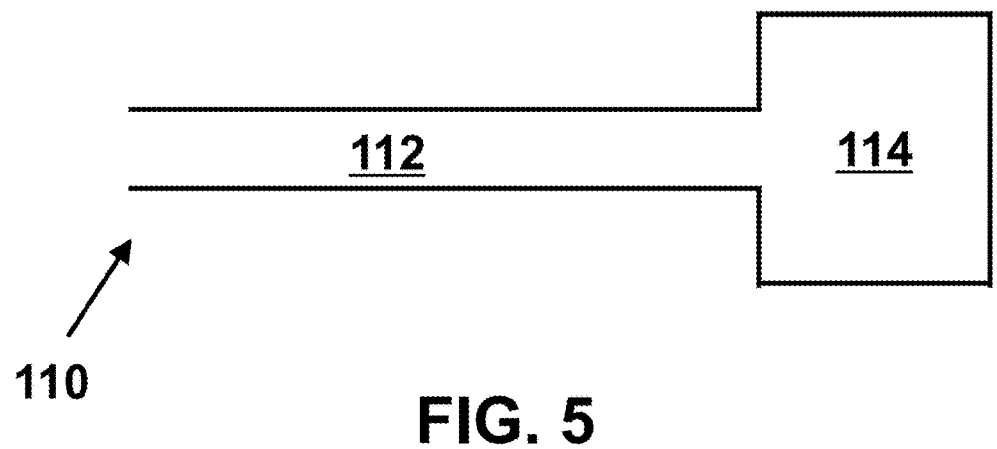
FIGS. 5-7 show different configurations of the device according to exemplary embodiments of the invention.

Calibration of the sensor can be done before implantation by immersing the sensor in a fluid with similar characteristics as the eye fluid (aqueous) and measuring the movement of fluid-gas interface in various fluid pressures. The calibration curve (e.g. FIG. 4) obtained by these measurements can serve for pressure calculation following implantation into the eye. Calibration can also be done post implantation by performing one or more intraocular pressure measurements done by clinically available techniques (such as the Goldman applanation tonometry). These measurements can serve for recalibration if a drift in pressure occurs over the years following implantation.

Figure 6:
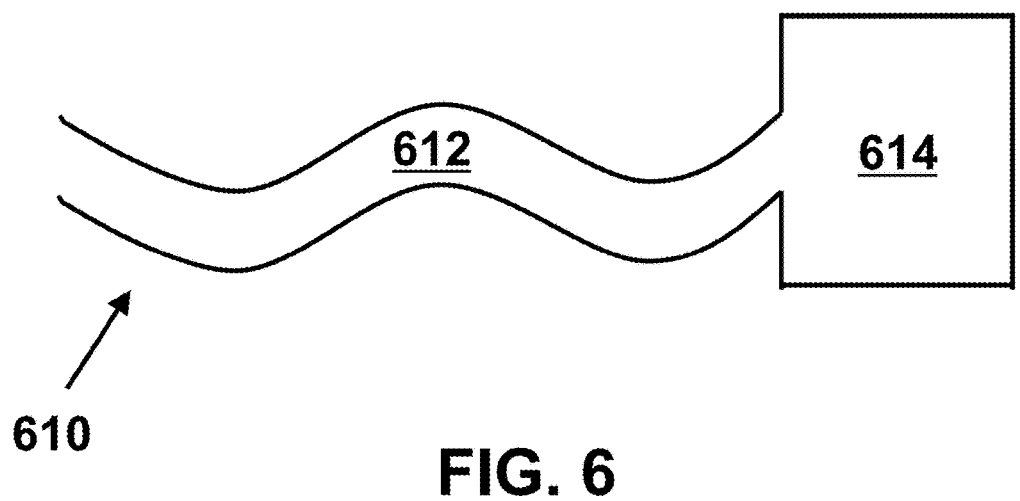
Figure 7:
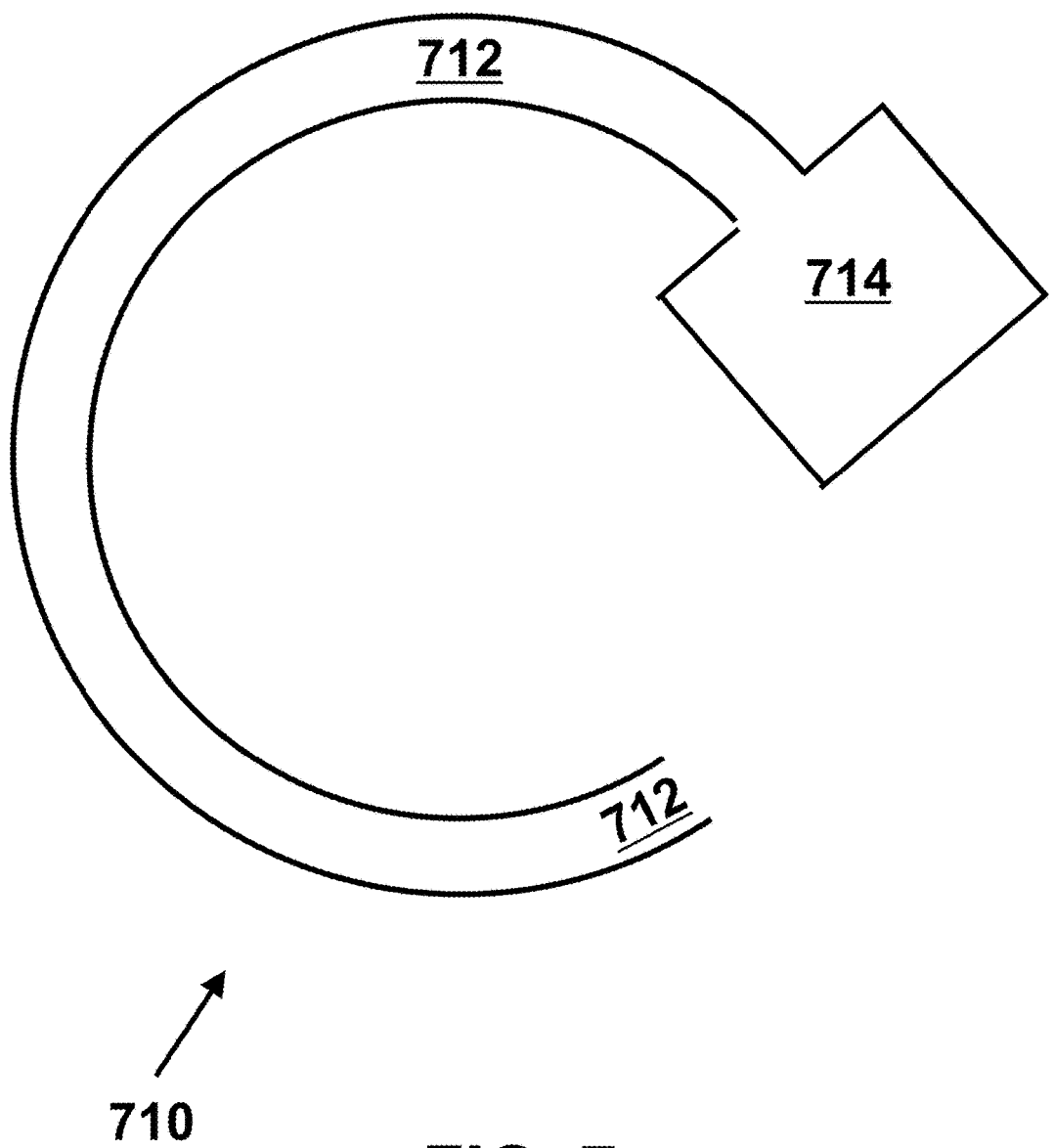
Figure 8:
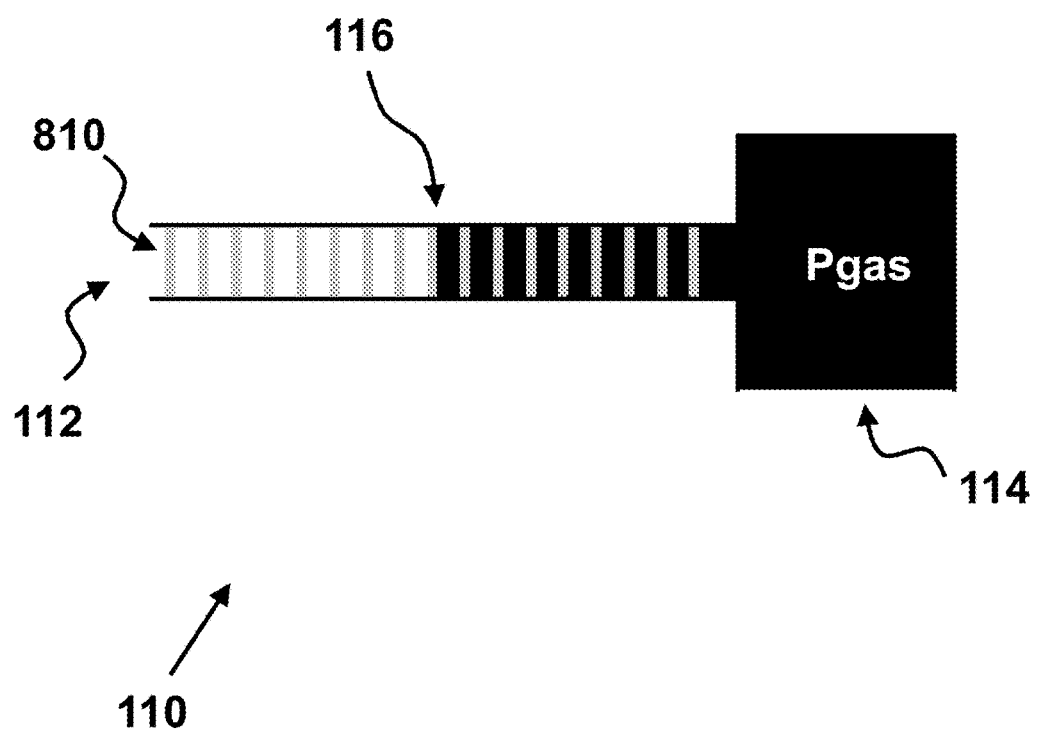
FIG. 8 shows positions or markings along the channel that can be imaged by a camera to measure intra-ocular pressures according to an exemplary embodiment of the invention.

The channels can be filled with one type of fluid or two types with different colors, where the interface between the two liquids can serve as a balance point for measuring IOP. For an example, the fluid could have low friction with the channels walls (e.g. oil) and with any type of gas. Low friction increases sensor sensitivity and decreases hysteresis phenomena. The position of the channels can be in the periphery of the implant (radius >2 mm) in such a way that they are hidden by the pupil and are exposed only when pupil is dilated (e.g. in darkness). The channels can be straight (FIGS. 1-3, 5 (with channel 112 and reservoir 114), serpentine (FIG. 6 with channel 612 and reservoir 614), or circular (FIG. 7 with channel 712 and reservoir 714) (radius of curvature larger than 1 mm and smaller than 12 mm). The inner diameter of the channels can be 1 µm to 300 µm and the channel length can be in the range of 500 µm to 30 mm. In another example, the inner diameter of the channel can have a 1 to 500 µm by 1 to 500 µm cross-section. The reservoir volume can be 500 by 500 by 300 µm³ or in terms of a range between 3 by 3 by 3 µm³ to 3 by 3 by 3 µm³. The ratio between the reservoir volume to channel cross section is in between 5 µm to $10^4$ µm. The channel walls should preferably have liquid and gas tight structures. Visible positions or marks 810 on the channels are used to enhance readout by the imaging device (FIG. 8).

The intraocular pressure could be transmitted to the intra-channel fluid through one or more openings in the channel or through a thin flexible membrane with a surface area in the range of 100 µm square to 100 mm square as described with respect to a second embodiment of the sensor.

Figure 9:
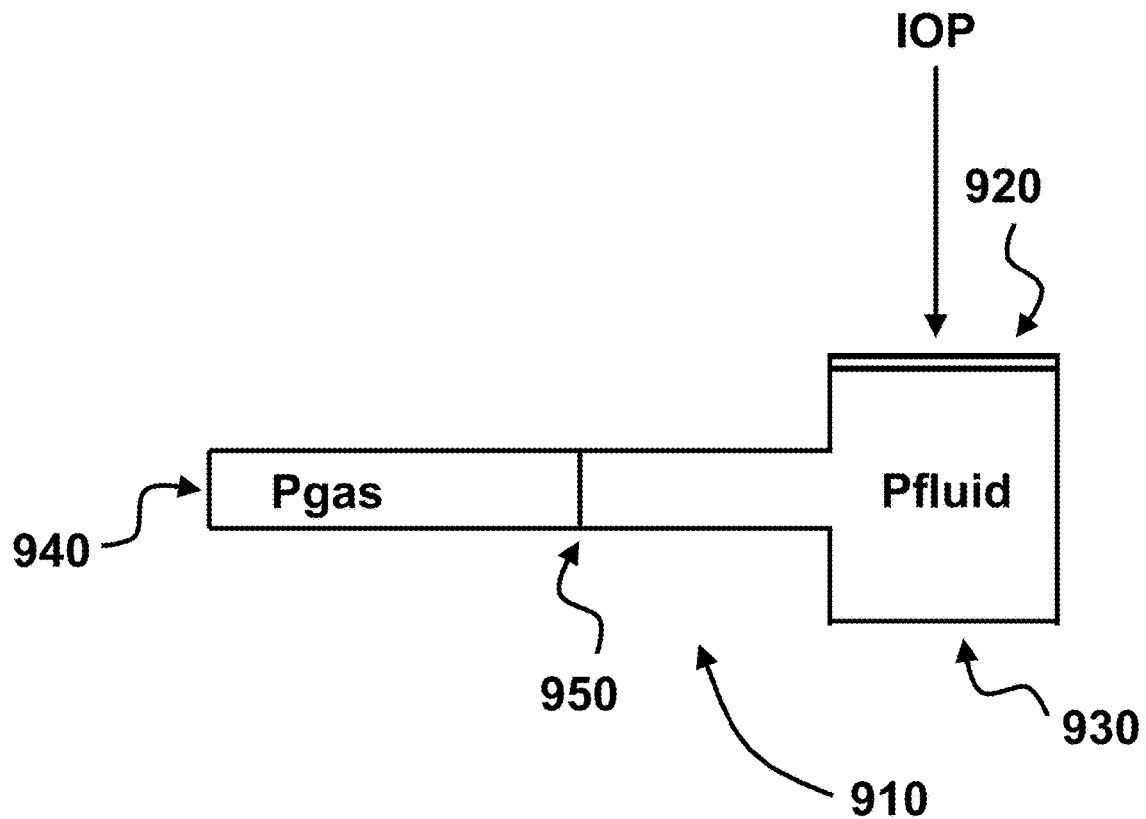
FIG. 9 shows according to an exemplary embodiment of the invention an IOP sensor with a flexible thin membrane covering a fluid filled reservoir, which is connected to a small cross section channel with a dead end.

In a second embodiment shown in FIG. 9, the IOP sensor 910 has a flexible thin membrane 920 covering a fluid filled reservoir 930, which is connected to a small cross section channel 940 with a dead end. Changes in the IOP cause shifts of fluid volume from the reservoir to the channels and therefore, a movement of the liquid-air (or other gasses) interface 950. Adding color to the fluid in the example could further enhance the visibility of the fluid column (not shown). Alternatively, two fluids with two different colors can be used.

A temperature sensor can be incorporated in the sensor and can be used for pressure correction. Temperature sensor could be incorporated near the IOP sensor or in a separate device.

The readout can be enhanced by using infrared sensitive camera and infrared illumination system which will not induced pupil constriction during imaging. The readout device can be composed on a cylinder or sphere shape construction that will block ambient light to enter the eye thus causing pupil dilation.

I.A Sensitivity Calculation

The following description pertains to sensitivity calculation for the first embodiment. When the capillary forces are ignored, the system is in equilibrium in the case of identical liquid and gas pressure values. A step function increase in the liquid pressure disturbs the equilibrium and results in a steady flow towards gas reservoir. The flow continues until the gas pressure becomes equal to liquid pressure. According to the ideal gas law:

$$P_{gas,init} \times V_{gas,init} = P_{gas,final} \times V_{gas,final}$$

When the initial gas pressure is assumed as 1 atmospheric pressure (760 mmHg), the sensitivity, defined as displacement of the interface position in response to 1 mmHg pressure change, can be derived from this as:

$$S = \frac{1}{761} \times \frac{V_{res}}{A_{ch}} \left(1 + \frac{V_{ch}}{V_{res}}\right)$$

where $V_{res}$, $A_{ch}$ and $V_{ch}$ are reservoir volume, channel cross section and channel volume respectively. When reservoir volume is much greater than the channel volume, sensitivity is simply dependent on the ratio between reservoir volume and channel cross section.

Figure 10:
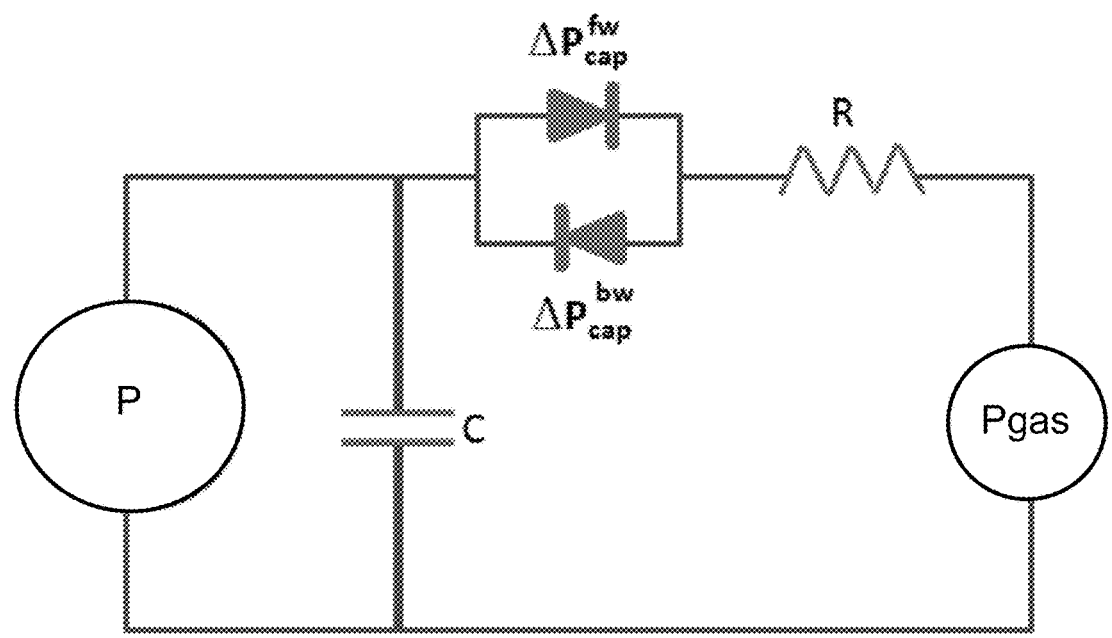
FIG. 10 shows a circuit according to an exemplary embodiment of the invention

In the more realistic case, the capillary effects and system compliance has to be taken into account. For a qualitative understanding of the role of these factors, we have used the equivalent circuit of the sensor inside a pressure chamber (circuit FIG. 10). The liquid pressure, P is the only variable in this circuit model and C is the capacitance due to device compliance, $\Delta P_{cap}^{fw,bw}$ are the capillary pressure drop in forward and backward directions, R is the fluidic resistance dependent on the channel geometry and $P_{gas}$ is the steady-state gas pressure.

It can be seen in the equivalent circuit model that, sensitivity (corresponds to fluidic flow and it is analogous to the integral of the current passing through the resistance R over time) will be reduced due to capillary pressure drop, $\Delta P_{cap}^{bw,fw}$ and capacitive effects of device compliance, C). We attribute the discrepancy between measured and theoretical sensitivity values to these factors. Besides the reduced sensitivity, the capillary effects cause a nonlinear behavior when they have positive values (hydrophobic surface) because in this case, pressure change required to move the interface has to be greater than $\Delta P_{cap}^{bw,fw}$ and thus indicated by a diode in the equivalent circuit. To eliminate the nonlinear behavior, the channel surfaces has to be rendered hydrophilic or equivalently channels has to be filled with a high lubricity liquid, in which cases $\Delta P_{cap}^{bw,fw}$ will become negative and degrading effects of the capillary pressure drop can be ignored.

I.B Implantation

In case where the sensor is embedded in an intraocular lens, it is implanted in the eye during a routine cataract surgery. The sensor can be implanted independently in the anterior chamber of the eye through a corneal or sclera wound and fixed into the iris or other part of the anterior chamber. Alternatively, the sensor can be implanted into the posterior chamber of the eye through corneal or sclera wound and fixed in the lens capsular bad or other locations.

With respect to the first embodiment, the sensor is filled with the desired gas in a gas chamber, which is held at an atmospheric pressure. Then the sensor is placed inside the desired liquid while it is still inside the gas chamber, therefore the gas is sealed inside the reservoir. Then the sensor is implanted into the eye as explained above. The surface energy between the liquid and sensor prevents the liquid from leaving the sensor.

II. Organ or Body Tissue Pressure Sensor

Figure 11:
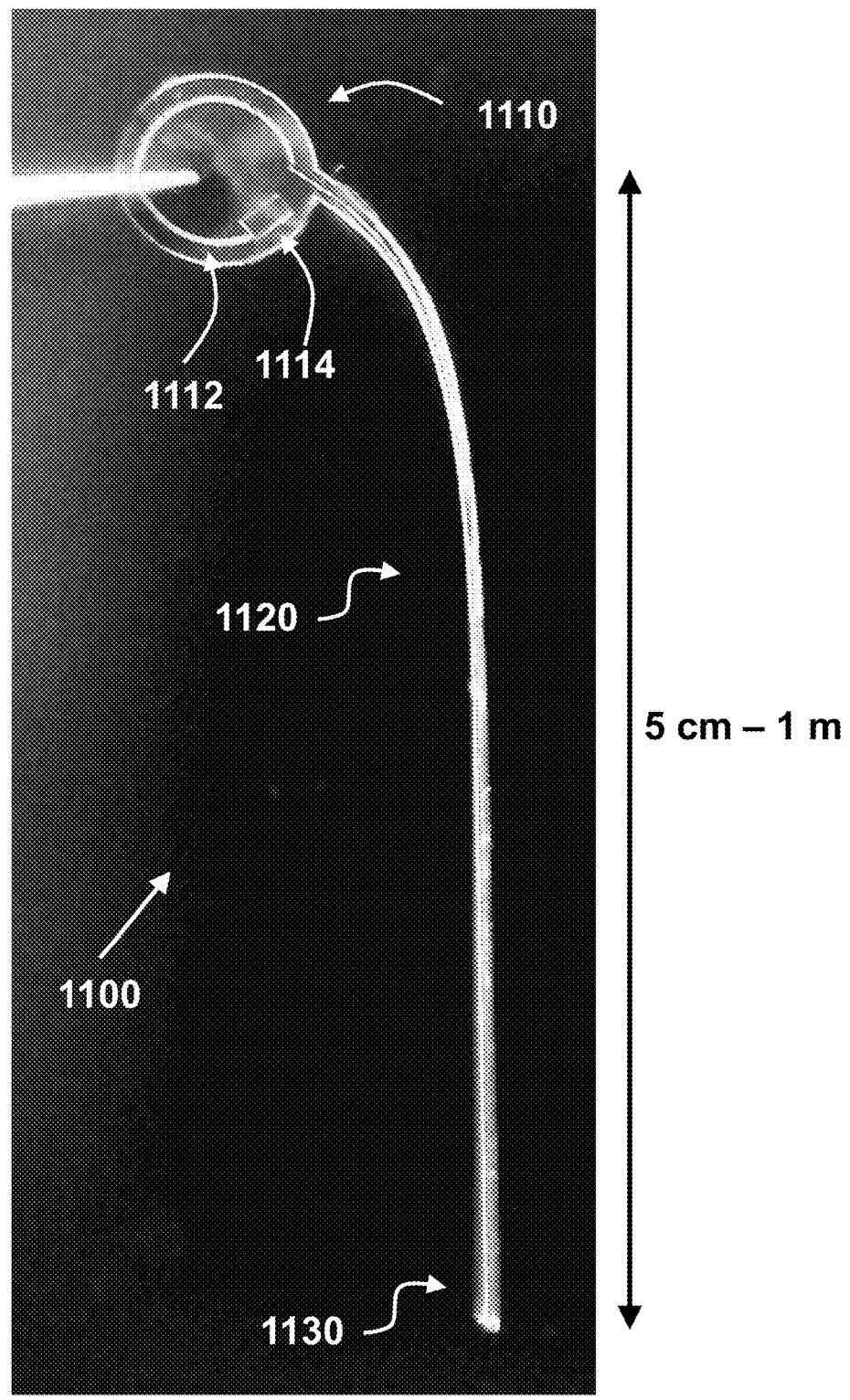
FIG. 11 shows according to an exemplary second embodiment of the invention a second embodiment distinguishing a sensing region and a tail region.
Figure 12:
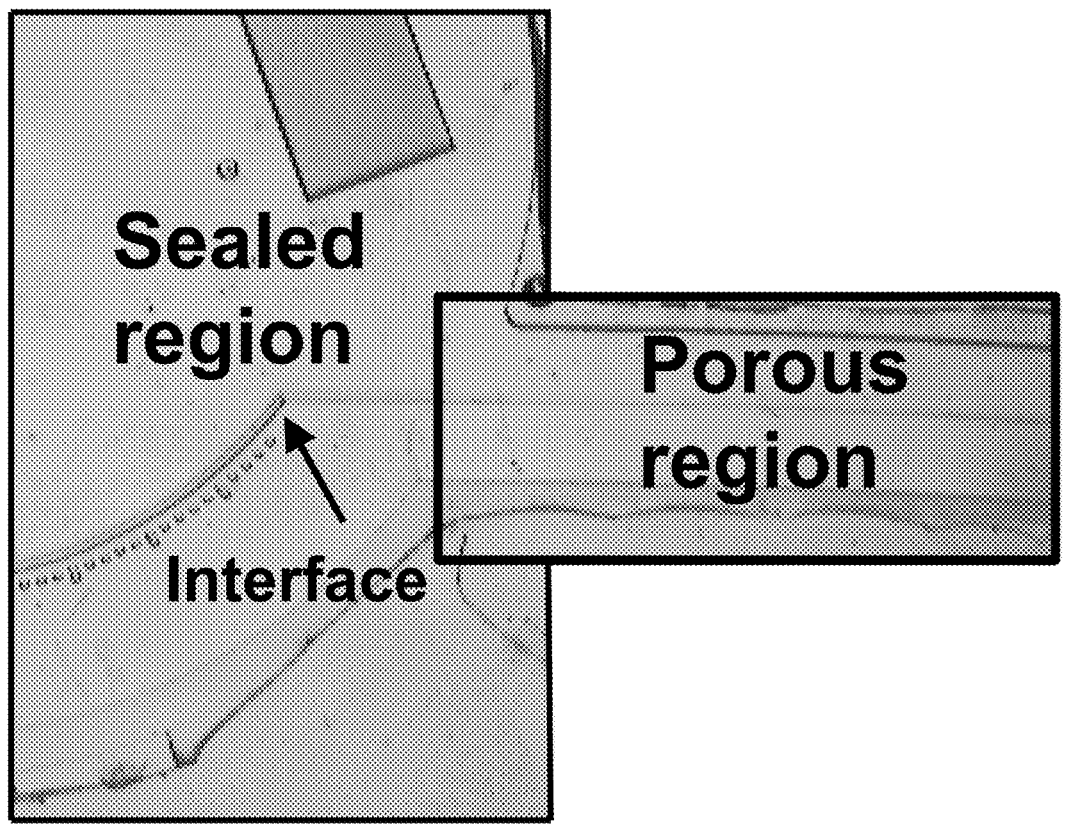
FIG. 12 shows according to an exemplary second embodiment of the invention the porous tail channel interfaced with the sensing region. The sensing region could be coated with parylene-C for hermetic sealing.
Figure 13:
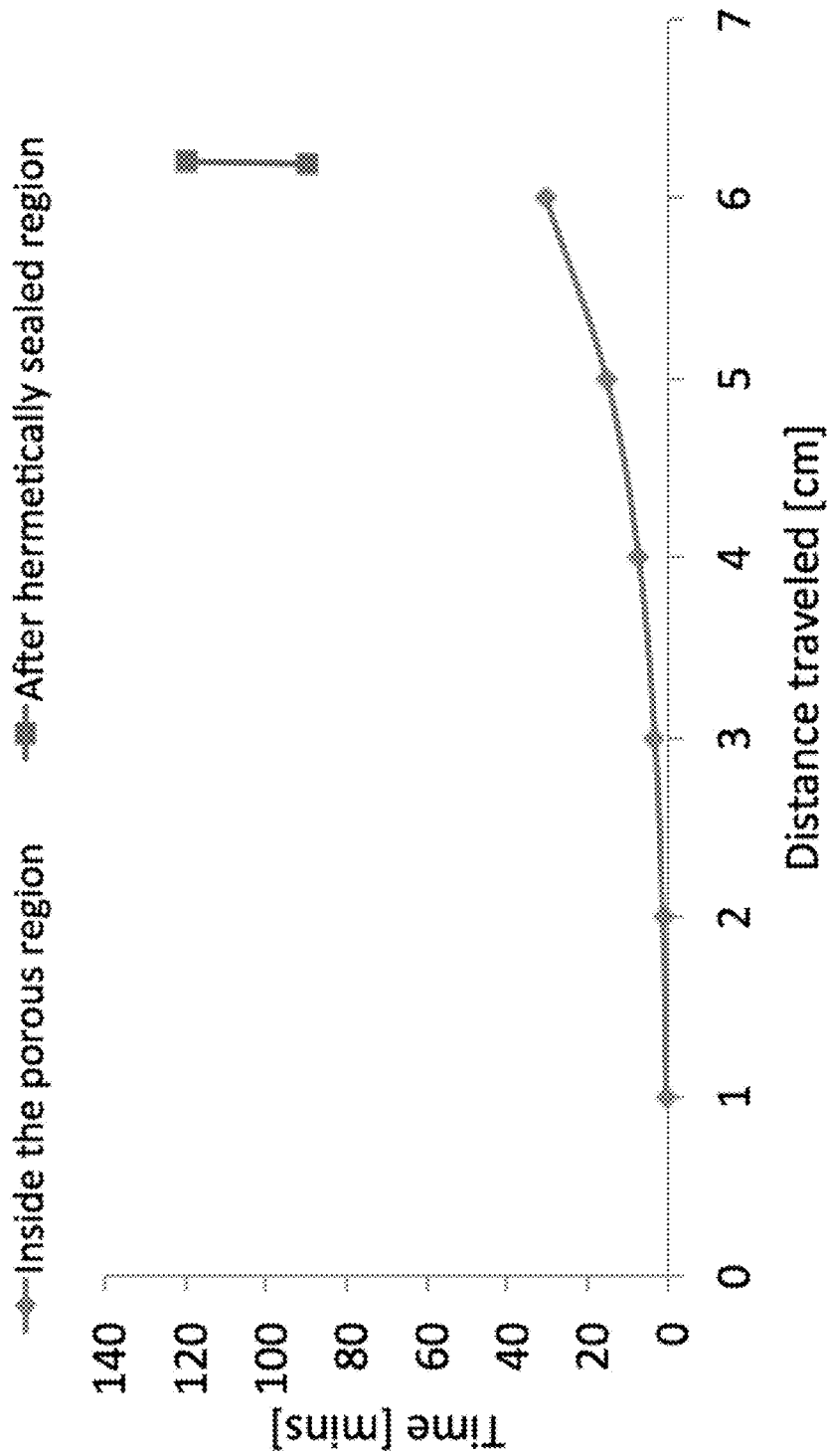
FIG. 13 shows according to an exemplary embodiment of the invention a tail section filled up with liquid in <1 hour and then stabilized inside the sensing region.
Figure 14A:
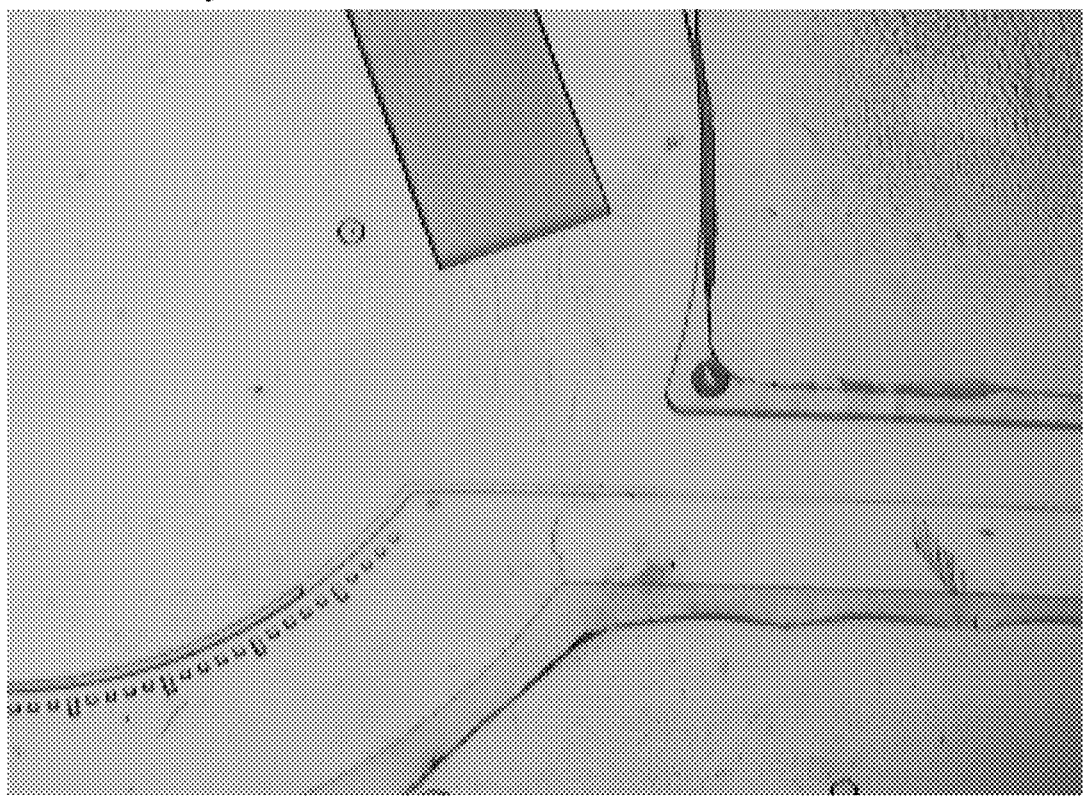
FIGS. 14A-C show according to an exemplary embodiment of the invention sensing of a baseline pressure (FIG. 14A), 10 mmHg pressure (FIG. 14B) and 20 mmHg pressure (FIG. 14C).
Figure 14B:
Figure 14C:
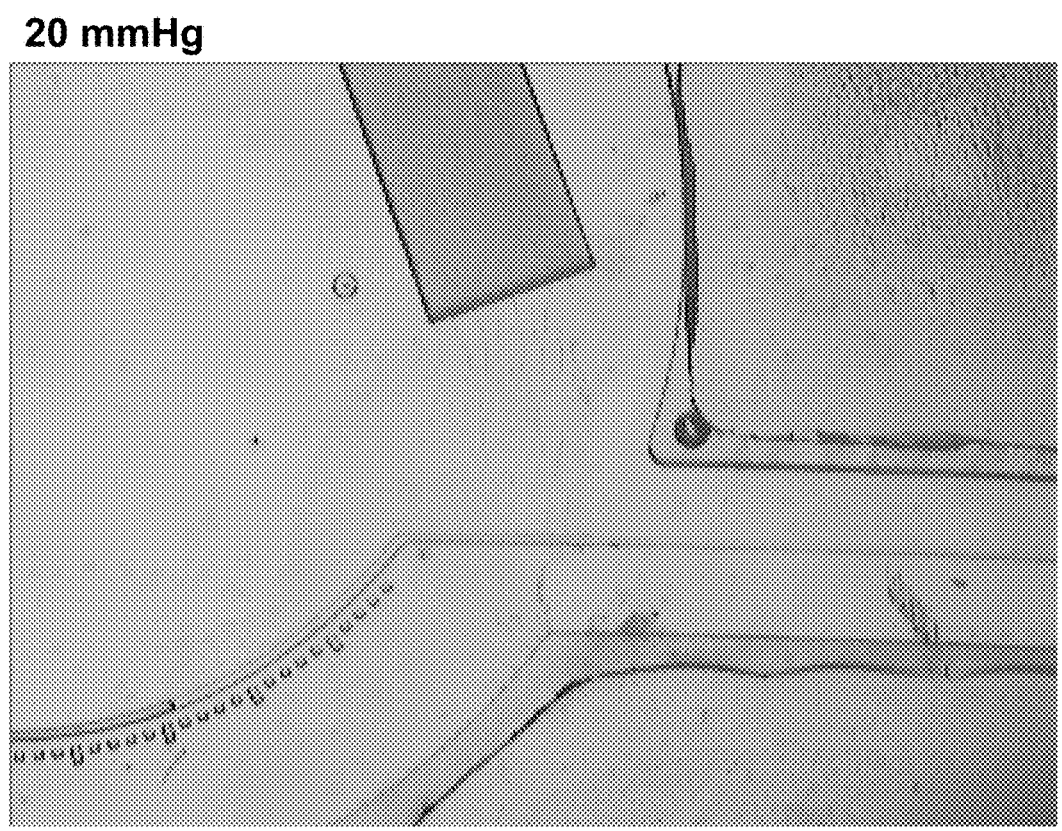
Figure 16:
FIG. 16 shows according to an exemplary embodiment of the invention a sensing region partially covered with a (in this case) chicken skin. The diffused fluorescence is not only due the skin tissue, but also due to the PDMS absorption of the dye.

In an example of the second embodiment of the invention as shown in FIG. 11, we have a passive microfluidic sensor 1100 for sensing pressure of an organ or body tissue. Such sensor distinguishes a "sensing region" 1110 and a "tail region" 1120. The sensing region includes a gas sealed channel 1112 as 112 or 712 in FIG. 1 and FIG. 7 respectively and a gas sealed reservoir chamber 1114 as 114 or 714 in FIG. 1 and FIG. 7. The gas/liquid interface is formed at the sensing region. The tail region 1130 is the extension of the sensing region, but as opposed to the parts of the sensing region, the tail region it is made of porous material and therefore has no capability to hold pressure. When implanted into the body cavities the liquid moves through the tail section into the sensing region. A liquid/gas interface (similar to 116 in e.g. FIGS. 1 and 3) is created at the sensing region. The tip of the tail is inserted into an organ or other tissue where the pressure could be measured. The sensing region could be implanted right under the tissue. In one example, the working liquid has a dye/nanoparticle/carbon nanotube, which will fluoresce at NIR or IR wavelengths.

The interface can be detected with a CCD camera on a smart phone or with a special IR camera. The interface position can be translated into a pressure value. The tail could be made out of a gas permeable material and the sensing region could be hermetically sealed, therefore the interface could move to the sensing region very quickly and stabilize in the sensing region.

Embodiments of the invention can find applications like intracranial pressure monitoring for patients suffering from hydrocephalus, blood pressure monitoring for hypertension patients, urinary tract/bladder monitoring, subcutaneous or intramuscular pressure monitoring etc.

Current methods in the art require complicated electronic and micro-electromechanical elements. They are not passive and consume energy thus require batteries. They are affected from the bodily electrolytes and electromagnetic noise (MR incompatible). The approach or technique presented in this invention is completely passive. There are no electrical components inside the body. The pressure measurement is done with a smartphone camera, decreasing the complexity and cost compared to current approaches. The pressure measurement is direct and the acquired data has a linear relation with the pressure (e.g. FIG. 4). The sensitivity can be increased dramatically by simple design changes such as by making the reservoir chamber much larger, if implanted into a larger organ.

Pressure sensing can be obtained using IR fluorescence from nanoparticles/dyes and can be measured by a camera through bodily tissue. The air permeable tail and hermetically sealed sensing region could be combined to transfer pressure from the organ to right under the skin tissue. Pressure sensing can also be measured by an ultrasound imaging system.

What is claimed is:

1. A pressure monitoring device, comprising:
   (a) a sensing channel with a first open end and a second open end, and an inner diameter;
   (b) a chamber connected to the second open end of the sensing channel;
   (c) a gas disposed in the chamber and disposed through the second open end up to a region of the sensing channel;
   (d) a fluid disposed from the first open end up to the region of the sensing channel establishing a fluid-gas equilibrium pressure interface within the sensing channel, wherein the inner diameter of the sensing channel is sized capable of holding the fluid within the sensing channel according to capillary forces; and
   (e) a porous tail channel connected to the first open end of the sensing channel and extending the sensing channel,
   wherein the pressure monitoring device is configured to be implantable in a body, wherein the sensing channel and the chamber would be implanted under the tissue, and wherein the porous tail channel would interface with a liquid in an organ or a body cavity, wherein the fluid in the sensing channel via the open end would fluidically interface with the liquid through the porous tail channel such that the liquid effects the fluid-gas equilibrium pressure interface which is used for measuring an organ pressure or a body cavity pressure based on an established equilibrium pressure interface between the liquid and the gas in the sensing channel.

2. The device as set forth in claim 1, wherein the sensing channel is made out of glass.

3. The device as set forth in claim 1, wherein positions along the sensing channel represent different measures of fluid-gas equilibrium pressure interfaces.

4. The device as set forth in claim 1, wherein the inner diameter of the sensing channel is 1 µm to 300 µm or a cross section of the inner diameter of the sensing channel is 1 to 500 µm by 1 to 500 µm.

5. The device as set forth in claim 1, wherein the sensing channel has a length of 500 µm to 100 mm.

6. The device as set forth in claim 1, wherein the porous tail channel has a length up to 1000 mm.

7. The device as set forth in claim 1, wherein the ratio between the gas reservoir volume to the sensing channel cross section is in between 5 µm to $10^4$ µm.

8. The device as set forth in claim 1, wherein the sensing channel or the pressure monitoring device is coated to prevent leakage of the gas and/or fluid.

9. The device as set forth in claim 1, wherein the sensing channel is a straight channel, a serpentine-like channel, or a circular-shaped channel.

10. The device as set forth in claim 1, wherein the fluid inside the sensing channel is mixed with IR fluorescent molecules.

11. A pressure monitoring system, comprising:
   (a) an organ monitoring device comprising:
      (i) a sensing channel with a first open end and a second open end, and an inner diameter;
      (ii) a chamber connected to the second open end of the sensing channel;
      (iii) a gas disposed in the chamber and disposed through the second open end up to a region of the sensing channel;
      (iv) a fluid disposed from the first open end up to the region of the sensing channel establishing a fluid-gas equilibrium pressure interface within the sensing channel, wherein the inner diameter of the sensing channel is sized capable of holding the fluid within the channel according to capillary forces;
      (v) a porous tail channel connected to the first open end of the sensing channel and extending the sensing channel,
      wherein the organ monitoring device is configured to be implantable in a body, wherein the sensing channel and the chamber would be implanted under the tissue, and wherein the porous tail channel would interface with a liquid in an organ or a body cavity, wherein the fluid in the sensing channel via the open end would fluidically interface with the organ liquid through the porous tail channel such that the liquid in the organ or the body cavity effects the fluid-gas equilibrium pressure interface which is used for measuring an organ pressure or a body cavity pressure based on an established equilibrium pressure interface between the liquid and the gas in the sensing channel;
   (b) an imaging device to obtain an image of the sensing channel; and
   (c) an image analysis computer program executable by a computer to quantify the organ pressure or the body cavity pressure from the obtained image and the established equilibrium pressure interface, and outputting the quantified organ pressure or the quantified body cavity pressure to a user.

12. The system as set forth in claim 11, wherein the sensing channel is made out of glass.

13. The system as set forth in claim 11, wherein positions along the sensing channel represent different measures of fluid-gas equilibrium pressure interfaces.

14. The system as set forth in claim 11, wherein the inner diameter of the sensing channel is 1 µm to 300 µm or a cross section of the inner diameter of the sensing channel is 1 to 500 µm by 1 to 500 µm.

15. The system as set forth in claim 11, wherein the sensing channel has a length of 500 µm to 100 mm.

16. The device as set forth in claim 11, wherein the porous tail channel has a length up to 1000 mm.

17. The system as set forth in claim 11, wherein the ratio between the gas reservoir volume to the sensing channel cross section is in between 5 µm to $10^4$ µm.

18. The system as set forth in claim 11, wherein the sensing channel or the organ monitoring device is coated to prevent leakage of the gas and/or fluid.

19. The system as set forth in claim 11, wherein the sensing channel is a straight channel, a serpentine-like channel, or a circular-shaped channel.

20. The system as set forth in claim 11, wherein the fluid inside the sensing channel is mixed with IR fluorescent molecules and fluorescence imaging for detection of the gas liquid interface is realized by an IR sensitive camera through a skin tissue as the imaging device.

21. The system as set forth in claim 11, the fluid inside the sensing channel is not mixed with any fluorescent molecules and an ultrasound imaging device is used for detection of the gas liquid interface through the skin tissue as the imaging device.

22. A method of monitoring organ or body cavity pressure, comprising:
   (a) implanting a pressure monitoring device in a body, wherein the pressure monitoring device comprises:

(i) a sensing channel with a first open end and a second open end, and an inner diameter;
(ii) a chamber connected to the second open end of the sensing channel;
(iii) a gas disposed in the chamber and disposed through the second open end up to a region of the sensing channel;
(iv) a fluid disposed from the first open end up to the region of the sensing channel establishing a fluid-gas equilibrium pressure interface within the sensing channel, wherein the inner diameter of the sensing channel is sized capable of holding the fluid within the channel according to capillary forces;
(vi) a porous tail channel connected to the first open end of the sensing channel and extending the sensing channel,
wherein the pressure monitoring device is configured to be implantable in a body, wherein the sensing channel and the chamber would be implanted under the tissue, and wherein the porous tail channel would interface with a liquid in an organ or a body cavity, wherein the fluid in the sensing channel via the open end would fluidically interface with the organ liquid or the body cavity liquid through the porous tail channel such that the organ liquid or the body cavity liquid effects the fluid-gas equilibrium pressure interface which is used for measuring an organ pressure or a body cavity pressure based on an established equilibrium pressure interface between the organ liquid or the body cavity liquid and the gas in the sensing channel;

(b) obtaining an image of the sensing channel with an imaging device; and
(c) quantifying the established equilibrium pressure interface into an organ pressure or a body cavity pressure from the obtained image using an image analysis computer program, and outputting the quantified organ pressure or the quantified body cavity pressure to a user.

* * * * *